United States Patent
Huang et al.

(10) Patent No.: US 12,421,325 B2
(45) Date of Patent: Sep. 23, 2025

(54) BLUMEA BALSAMIFERA MONOTERPENE SYNTHASE BBTPS3 AND RELATED BIOLOGICAL MATERIALS THEREOF AND USE THEREOF

(71) Applicant: Sichuan Honghe Biotechnology Co., Ltd., Nanchong (CN)

(72) Inventors: Luqi Huang, Beijing (CN); Ping Su, Beijing (CN); Rui Ma, Beijing (CN); Wei Gao, Beijing (CN); Guanghong Cui, Beijing (CN); Baolong Jin, Beijing (CN); Yating Hu, Beijing (CN); Jichen Bao, Beijing (CN); Juan Guo, Beijing (CN)

(73) Assignee: Sichuan Honghe Biotechnology Co., Ltd. (CN)

( * ) Notice: Subject to any disclaimer, the term of this patent is extended or adjusted under 35 U.S.C. 154(b) by 707 days.

(21) Appl. No.: 17/636,720

(22) PCT Filed: Aug. 20, 2020

(86) PCT No.: PCT/CN2020/110234
§ 371 (c)(1),
(2) Date: Feb. 18, 2022

(87) PCT Pub. No.: WO2021/032159
PCT Pub. Date: Feb. 25, 2021

(65) Prior Publication Data
US 2022/0348691 A1 Nov. 3, 2022

(30) Foreign Application Priority Data
Aug. 21, 2019 (CN) .......................... 201910775971.6

(51) Int. Cl.
| | | |
|---|---|---|
| C12P 7/02 | (2006.01) |
| C07K 19/00 | (2006.01) |
| C12N 9/88 | (2006.01) |
| C12N 9/92 | (2006.01) |
| C12N 15/10 | (2006.01) |
| C12N 15/62 | (2006.01) |
| C12N 15/81 | (2006.01) |
| C12N 15/82 | (2006.01) |

(52) U.S. Cl.
CPC .............. *C07K 19/00* (2013.01); *C12N 15/10* (2013.01); *C12N 15/62* (2013.01); *C12N 15/81* (2013.01)

(58) Field of Classification Search
CPC ........... C12N 9/88; C12N 15/10; C07K 19/00
See application file for complete search history.

(56) References Cited

FOREIGN PATENT DOCUMENTS

| CN | 103525848 A | 1/2014 |
| CN | 108138168 A | 6/2018 |
| WO | 2013187754 A1 | 12/2013 |

OTHER PUBLICATIONS

Guan, L et al., "Cloning and Analysis of Geranyl Pyrophosphate Synthase (GPPS) Sequence of *Blumea balsamifera* L. DC on Transcriptome Information", "Chinese Journal of Tropical Crops", Dec. 2016, pp. 901-909, vol. 37, No. 5 (Providing English Abstract Only).
International Search Report for PCTCN2020110234 dated Nov. 26, 2020, 3 pgs.
NCBI Reference Sequence, "R-linalool synthase QH1, chloroplastic [Lactuca sativa]", Aug. 2021, XP_023767623.1. 1 pg.
Search Report dated Jan. 17, 2022 from Office Action for Chinese Application No. 201910775971.6 issued Jan. 28, 2022. 1 pg.

*Primary Examiner* — Maryam Monshipouri
(74) *Attorney, Agent, or Firm* — Lerner David LLP

(57) ABSTRACT

Provided are a *Blumea balsamifera* monoterpene synthase BbTPS3 and related biological materials thereof and use thereof. BbTPS3 is: A1) a protein having the amino acid sequence shown in SEQ ID NO: 2; A2) a fusion protein obtained by linking protein-tags at the N-terminus or/and the C-terminus of the protein shown in SEQ ID NO: 2; and A3) a protein having at least 90% identity and the same function as the protein shown in A1), which is obtained by performing substitution and/or deletion and/or addition of one or more amino acid residues on the amino acid sequence shown in SEQ ID NO: 2. BbTPS3 can catalyze GPP to form l-borneol, and can be used to regulate and produce plant monoterpene compounds and cultivate *Blumea balsamifera* (L.) DC.

8 Claims, 3 Drawing Sheets
Specification includes a Sequence Listing.

SEQUENCE LISTING

<160> NUMBER OF SEQ ID NOS: 2

<210> SEQ ID NO 1
<211> LENGTH: 1671
<212> TYPE: DNA
<213> ORGANISM: Blumea balsamifera (L.) DC.

<400> SEQUENCE: 1

```
atggttggat ttcaaaaaca ctcatgttca acacaagtta cagaacccat aatcagaaga      60
tcagcaaact atccaccttc gagatggtcc tatgaggttc tccaatcggt cactaacaac     120
tatgtgggtg aaaaatacaa gataacgtca aataatttga aagaaagagt gaggatgatg     180
atttctaaag acactgcaat gaaaaatcct ttgagcatgc tcgaattagt tgatgatttg     240
caaagacttg gagtatccta tcatttcaaa gatgaaataa gcaatgtgct aaagatgata     300
tatagttatc actatgaagc tcataataat tggaatacat tggatcttaa tcttaaagcc     360
cttggcttta gactcttaag acaacatggc tatcatatcc cacaagaaat tttaaggac      420 atcacggatg agtcaggaaa catcaaggcg agtgtacaag acgactttgt agcgatgctt     480
aacttgtatg aggcttcatt ttacgctgta gatgatgaaa atatcatgga tgaagcaagg     540
gaattcacga gaaaatgcct caaagagaaa ttagaaaaga ataatattgt taataaaagt     600
ataatgatgt taataagcca tgccttggag catccattgc tttttaggat cccaaggttt     660
gagtcagtat ggtttataga agcatacaaa acgagggatg acatgatacc attgttgtta     720
gagttcgcgg tcttagatta caatattttg caaggaattc accaagaaga tctcaagcac     780
gtatcaaagt ggtgggttgg tctacattgg atcaagaatc ttgagtttgc tcgagactca     840
atggtggagt gtttttcgtg gtctgtgggg gcaaaccccg aaccttcatt tagtgttcta     900
aggagaaata tgacaaagaa tctaacattc acaagtgtgt tagacgatgt ttatgatgtg     960
tatggtactt tggatgaact cgaacaattc accgaagcag tgagaagatg ggacatgaat    1020
gcggccgaag gacttcctga ttacatgagg atatgtttca tgggattata caacacaatc    1080
aatgagatgg catacaatac ctttataaac cataaatctt ttgtcatacc ttatttgaga    1140
aaagtgtgga cagaattttg tgaggcaaac cttcaggagg cacgatggta ttatagtgga    1200
tatatcccaa catttgagga atacttgaag acctcagtaa ttactgtagc agttcccgta    1260
atagttttgg ctgcttattt cttggaagca aatgatctta gtaacgaggc cttcgataat    1320
gttattcact catcagctat aattctacgc cttactgatg accagggaac ttcagaggct    1380
gagcttgcaa gaggtgatgt tccaaaatca gtccagtgct acatgaatga aaccggtgct    1440
tctagaaatg aagctatagc atatatgaag agattaatca taaatgcaca taagacgata    1500
aataaagaaa gaatggcatg taaatctcct actttgcaga tatttatgga atgcgcaaca    1560
```

```
aaccttggtc ggattgggca cgttacatat gaccacgggg acatgtttgg tgtaccagat    1620
gattcccatc aatctcatca taactcatta cttttgaagc ctaaaaccta g             1671
```

<210> SEQ ID NO 2
<211> LENGTH: 556
<212> TYPE: PRT
<213> ORGANISM: Blumea balsamifera (L.) DC.

<400> SEQUENCE: 2

```
Met Val Gly Phe Gln Lys His Ser Cys Ser Thr Gln Val Thr Glu Pro
1               5                   10                  15

Ile Ile Arg Arg Ser Ala Asn Tyr Pro Pro Ser Arg Trp Ser Tyr Glu
            20                  25                  30

Val Leu Gln Ser Val Thr Asn Asn Tyr Val Gly Glu Lys Tyr Lys Ile
        35                  40                  45

Thr Ser Asn Asn Leu Lys Glu Arg Val Arg Met Met Ile Ser Lys Asp
    50                  55                  60

Thr Ala Met Lys Asn Pro Leu Ser Met Leu Glu Leu Val Asp Asp Leu
65                  70                  75                  80

Gln Arg Leu Gly Val Ser Tyr His Phe Lys Asp Glu Ile Ser Asn Val
                85                  90                  95

Leu Lys Met Ile Tyr Ser Tyr His Tyr Glu Ala His Asn Asn Trp Asn
            100                 105                 110

Thr Leu Asp Leu Asn Leu Lys Ala Leu Gly Phe Arg Leu Leu Arg Gln
        115                 120                 125

His Gly Tyr His Ile Pro Gln Glu Ile Phe Lys Asp Ile Thr Asp Glu
    130                 135                 140

Ser Gly Asn Ile Lys Ala Ser Val Gln Asp Asp Phe Val Ala Met Leu
145                 150                 155                 160

Asn Leu Tyr Glu Ala Ser Phe Tyr Ala Val Asp Asp Glu Asn Ile Met
                165                 170                 175

Asp Glu Ala Arg Glu Phe Thr Arg Lys Cys Leu Lys Glu Lys Leu Glu
            180                 185                 190

Lys Asn Asn Ile Val Asn Lys Ser Ile Met Met Leu Ile Ser His Ala
        195                 200                 205

Leu Glu His Pro Leu Leu Phe Arg Ile Pro Arg Phe Glu Ser Val Trp
    210                 215                 220

Phe Ile Glu Ala Tyr Lys Thr Arg Asp Asp Met Ile Pro Leu Leu Leu
225                 230                 235                 240

Glu Phe Ala Val Leu Asp Tyr Asn Ile Leu Gln Gly Ile His Gln Glu
                245                 250                 255

Asp Leu Lys His Val Ser Lys Trp Trp Val Gly Leu His Trp Ile Lys
            260                 265                 270

Asn Leu Glu Phe Ala Arg Asp Ser Met Val Glu Cys Phe Ser Trp Ser
        275                 280                 285

Val Gly Ala Asn Pro Glu Pro Ser Phe Ser Val Leu Arg Arg Asn Met
    290                 295                 300

Thr Lys Asn Leu Thr Phe Thr Ser Val Leu Asp Asp Val Tyr Asp Val
305                 310                 315                 320

Tyr Gly Thr Leu Asp Glu Leu Glu Gln Phe Thr Glu Ala Val Arg Arg
                325                 330                 335

Trp Asp Met Asn Ala Ala Glu Gly Leu Pro Asp Tyr Met Arg Ile Cys
            340                 345                 350
```

```
Phe Met Gly Leu Tyr Asn Thr Ile Asn Glu Met Ala Tyr Asn Thr Phe
        355                 360                 365

Ile Asn His Lys Ser Phe Val Ile Pro Tyr Leu Arg Lys Val Trp Thr
    370                 375                 380

Glu Phe Cys Glu Ala Asn Leu Gln Glu Ala Arg Trp Tyr Tyr Ser Gly
385                 390                 395                 400

Tyr Ile Pro Thr Phe Glu Glu Tyr Leu Lys Thr Ser Val Ile Thr Val
                405                 410                 415

Ala Val Pro Val Ile Val Leu Ala Ala Tyr Phe Leu Glu Ala Asn Asp
            420                 425                 430

Leu Ser Asn Glu Ala Phe Asp Asn Val Ile His Ser Ser Ala Ile Ile
        435                 440                 445

Leu Arg Leu Thr Asp Asp Gln Gly Thr Ser Glu Ala Glu Leu Ala Arg
    450                 455                 460

Gly Asp Val Pro Lys Ser Val Gln Cys Tyr Met Asn Glu Thr Gly Ala
465                 470                 475                 480

Ser Arg Asn Glu Ala Ile Ala Tyr Met Lys Arg Leu Ile Ile Asn Ala
                485                 490                 495

His Lys Thr Ile Asn Lys Glu Arg Met Ala Cys Lys Ser Pro Thr Leu
            500                 505                 510

Gln Ile Phe Met Glu Cys Ala Thr Asn Leu Gly Arg Ile Gly His Val
        515                 520                 525

Thr Tyr Asp His Gly Asp Met Phe Gly Val Pro Asp Asp Ser His Gln
        530                 535                 540

Ser His His Asn Ser Leu Leu Leu Lys Pro Lys Thr
545                 550                 555
```

BLUMEA BALSAMIFERA MONOTERPENE SYNTHASE BBTPS3 AND RELATED BIOLOGICAL MATERIALS THEREOF AND USE THEREOF

CROSS-REFERENCE TO RELATED APPLICATION

This application is a U.S. national stage application, filed under 35 U.S.C. § 371, of International Patent Application No. PCT/CN2020/110234, filed on Aug. 20, 2020, which claims priority from Chinese Application No. 201910775971.6, filed Aug. 21, 2019, all of which is incorporated by reference herein in its entirety.

TECHNICAL FIELD

The present invention belongs to the field of medicinal plant genetic engineering, and more particularly, relates to *Blumea balsamifera* monoterpene synthase BbTPS3 and related biological materials thereof and use thereof.

BACKGROUND OF THE INVENTION

*Blumea balsamifera* (L.) DC., first recorded in *Kaibao Bencao*, is the only plant source of "blumea camphor" (a kind of borneol) recorded in *Pharmacopoeia of People's Republic of China* (2020 Edition) (National Pharmacopoeia Committee. Pharmacopoeia of People's Republic of China [M]. Beijing: China Medical Science Press, 2020.). According to the records in the traditional Chinese medicine dictionary, *Blumea balsamifera* (L.) DC. is acrid, bitter and mild, and has the functions of anti-hypertension, angiectasis and diuresis (Nanjing University of Traditional Chinese Medicine. Traditional Chinese medicine dictionary[M]. Shanghai: Science and Technology Press, 2006.), the plants of *Blumea balsamifera* (L.) DC. are mainly distributed in the southeast of Yunnan province, the southwest of Guangxi province, Guangdong, Guizhou, Hainan, Fujian and Taiwan and other provinces, and *Blumea balsamifera* (L.) DC. has a long medicinal history in China's minority areas such as Miao, Zhuang, Li and Yao, and is an important folk medicine.

(−)-Borneol (l-borneol), also known as blumea camphor, is an important secondary metabolite of *Blumea balsamifera* (L.) DC. and a main active medical ingredient of *Blumea balsamifera* (L.) DC. According to the records in *Pharmacopoeia of People's Republic of China* (2020 Edition), (−)-borneol has the functions of resuscitation induction, heat clearing and pain alleviation, and is used in coma due to fever, syncope with convulsion, phlegm syncope due to stroke, sudden convulsion due to qi-stasis, coma due to noxious pathogen attack, hot eyes, aphtha, sore throat and otorrhea. Modern pharmacological studies have proved that l-borneol has the functions of anti-inflammation, anti-oxidation, pain alleviation, medicine absorption promotion and refreshing. l-Borneol can significantly improve cerebral ischemia and hypoxia under physiological and pathological states, thus playing a protective role in brain, which may be the pharmacodynamic basis of its refreshing function. l-Borneol is capable of quickly penetrating through the blood-brain barrier, is distributed in brain tissues, improves the damage to the tight junction of the blood-brain barrier, and is capable of resisting the damage of free radicals to brain tissues (Hui Tian. Comparative research on mechanism of neuroprotective effect and influence of blood-brain barrier between l-borneolum and borneolum syntheticum [D]. Chengdu: Chengdu University of Traditional Chinese Medicine. 2013). l-Borneol has significant effects of anti-myocardial ischemia and hypoxia and anti-cerebral ischemia and hypoxia of mouse (Cheng Jiang, Gui Yang. Effect of l-borneol on anoxia-tolerance in mice [J]. Sichuan Journal of Physiological Sciences. 2012, 34(2): 63-65).

It is a potential way to develop new medicines from the active ingredients of Traditional Chinese Medicine. However, due to the slow growth of plants, the content of effective ingredients in plants is low, and the extraction and separation process is cumbersome and easy to cause environmental pollution, the development is greatly limited. (−)-Borneol belongs to a bicyclic monoterpene compound, the cytosolic MVA pathway and the plastidial 2-C-methyl-$_D$-erythritol 4-phosphate (MEP) pathway produce isopentenyl pyrophosphate (IPP) and its isomer dimethylallyl pyrophosphate (DMAPP), which are general substrates of terpenoids, and they produce the monoterpene precursor geranyl diphosphate (GPP), which is cyclized by the monoterpene synthase and is then dephosphorylated to produce (−)-borneol.

At present, there is no relevant research on the key enzyme genes with the ability to synthesize monoterpenes from *Blumea balsamifera* (L.) DC.

SUMMARY OF THE INVENTION

The technical problem to be solved by the present invention is to obtain a new *Blumea balsamifera* monoterpene synthase which participates in the synthesis of monoterpenes, so as to synthesize or prepare (−)-borneol.

In order to solve the above problem, the present invention provides a protein first, and the protein is BbTPS3, which is derived from *Blumea balsamifera* (L.) DC., named as *Blumea balsamifera* monoterpene synthase BbTPS3, and represented by any one of the followings:

A1) a protein having the amino acid sequence shown in SEQ ID NO: 2 in the sequence listing;

A2) a fusion protein obtained by linking protein-tags at the N-terminus or/and the C-terminus of the protein shown in SEQ ID NO: 2 in the sequence listing;

A3) a protein having at least 90% identity and the same function as the protein shown in A1), which is obtained by performing substitution and/or deletion and/or addition of one or more amino acid residues on the amino acid sequence shown in SEQ ID NO: 2 in the sequence listing.

Among them, SEQ ID NO: 2 consists of 556 amino acid residues.

The above protein can be artificially synthesized or obtained by first synthesizing their encoding genes and then performing biological expression.

In the above protein, the protein-tag refers to a polypeptide or protein subjected to fusion expression with a target protein by using in-vitro DNA recombination technology, so as to facilitate expression, detection, tracing and/or purification of the target protein. The protein-tag can be a Flag tag, a His tag, a MBP tag, a HA tag, a myc tag, a GST tag and/or a SUMO tag.

In the above protein, the identity refers to an identity of amino acid sequences. The identity of amino acid sequences can be determined by using a homology search site on the internet, such as the BLAST webpage of the NCBI homepage website. For example, in advanced BLAST2.1, by using blastp as the program, the Expect value is set to be 10, all Filters are set to be OFF, BLOSUM62 is used as Matrix, Gap existence cost, Per residue gap cost and Lambda ratio are respectively set to be 11, 1 and 0.85 (default values), an identity of a pair of amino acid sequences is searched for calculation, and then an identity value (%) can be obtained.

In the above protein, the at least 90% identity can be at least 91%, 92%, 95%, 96%, 98%, 99% or 100% identity.

The related biological material of BbTPS3 is also within the protection scope of the present invention.

The related biological material of BbTPS3 provided by the present invention is represented by any one of the following A1) to A12):

A1) a nucleic acid molecule encoding BbTPS3;

A2) an expression cassette containing the nucleic acid molecule of A1);

A3) a recombinant vector containing the nucleic acid molecule of A1);

A4) a recombinant vector containing the expression cassette of A2);

A5) a recombinant microorganism containing the nucleic acid molecule of A1);

A6) a recombinant microorganism containing the expression cassette of A2);

A7) a recombinant microorganism containing the recombinant vector of A3);

A8) a recombinant microorganism containing the recombinant vector of A4);

A9) a transgenic plant cell line containing the nucleic acid molecule of A1);

A10) a transgenic plant cell line containing the expression cassette of A2);

A11) a transgenic plant cell line containing the recombinant vector of A3);

A12) a transgenic plant cell line containing the recombinant vector of A4).

In the above biological material, the nucleic acid molecule of A1) is represented by the following B1) or B2) or B3):

B1) a DNA molecule shown in SEQ ID NO: 1 in the sequence listing;

B2) a DNA molecule encoding the sequence shown in SEQ ID NO: 1 in the sequence listing; and B3) a DNA molecule which is hybridized with the DNA molecule defined in B1) or B2) under a strict condition and encodes BbTPS3.

Among them, SEQ ID NO: 1 in the sequence listing consists of 1671 nucleotides, and encodes the protein shown in SEQ ID NO: 2.

The strict condition refers to performing hybridization at 68° C. in 2×SSC buffer with 0.1% SDS, and washing the membrane twice for 5 minutes each, and then performing hybridization at 68° C. in 0.5×SSC buffer with 0.1% SDS, and washing the membrane twice for 15 minutes each.

Among them, the nucleic acid molecule can be DNA, such as cDNA, genomic DNA or recombinant DNA, and the nucleic acid molecule can also be RNA, such as mRNA or hnRNA.

In the above biological material, the expression cassette containing the nucleic acid molecule encoding BbTPS3 of A2) (Bbtps3 gene expression cassette) refers to a DNA molecule capable of expressing BbTPS3 in a host cell, and the DNA molecule not only can comprise a promoter for promoting Bbtps3 transcription, but also can comprise a terminator for terminating Bbtps3 transcription. Further, the expression cassette can further comprise an enhancer sequence.

In the above biological material, the vector can be a plasmid, a cosmid, a phage or a virus vector.

In the above biological material, the microorganism can be a yeast, a bacterium, an alga or a fungus, such as *Agrobacterium tumefaciens.*

In the above biological material, none of the transgenic plant cell lines, the transgenic plant tissues and the transgenic plant organs comprise propagation materials.

The present invention further provides use of the above protein or the above related biological material.

The use is specifically represented by the followings:

1) use of the above protein as a monoterpene synthase;

2) use of the above related biological material in preparing a monoterpene synthase;

3) use of the above protein or the above related biological material in preparing or synthesizing a monoterpene compound; and 4) use of the above protein or the above related biological material in catalyzing the formation of (−)-borneol from geranyl pyrophosphate.

In the above use, the monoterpene compound is (−)-borneol.

The present invention also provides a method for preparing BbTPS3.

In the present invention, the method for preparing BbTPS3 comprises the steps of: introducing the encoding gene of BbTPS3 into a recipient microorganism to obtain a recombinant microorganism expressing BbTPS3, and culturing the recombinant microorganism to express BbTPS3.

In the above method, the recipient microorganism is a prokaryotic microorganism. Specifically, the prokaryotic microorganism is *Escherichia coli*. More specifically, the *Escherichia coli* is the *Escherichia coli* Transetta (DE3).

In the above method, the encoding gene of BbTPS3 can be introduced into the *Escherichia coli* Transetta (DE3) through a recombinant plasmid pET32a::BbTPS3; and the recombinant plasmid pET32a::BbTPS3 is obtained by constructing the Bbtps3 gene shown in SEQ ID NO: 1 at the BamHI site of a pET32a(+) vector, and the rest sequence of the pET32a(+) vector remains unchanged.

The present invention further provides a method for preparing (−)-borneol.

In the present invention, the method for preparing (−)-borneol comprises the step of catalyzing geranyl pyrophosphate (GPP) with BbTPS3.

In the above method, it is also necessary to add an enzymatic buffer in the catalytic process, and the enzymatic buffer consists of HEPES, $MgCl_2$ and DTT;

the concentration of HEPES in the enzymatic buffer is 25 mM;

the concentration of $MgCl_2$ in the enzymatic buffer is 5 mM;

the concentration of DTT in the enzymatic buffer is 5 mM; and the pH of the enzymatic buffer is 7.0.

In the above method, the method further comprises the step of performing a dephosphorylation reaction on the obtained enzymatic reaction product after catalyzing geranyl pyrophosphate (GPP) with BbTPS3, to obtain (−)-borneol.

The present invention further provides a method for biosynthesizing (−)-borneol.

The method for biosynthesizing (−)-borneol of the present invention comprises the steps of: introducing the encoding gene of BbTPS3 into *Saccharomyces cerevisiae* to obtain recombinant *Saccharomyces cerevisiae*, and fermenting the recombinant *Saccharomyces cerevisiae* to obtain (−)-borneol.

In the above method, the yeast *Saccharomyces cerevisiae* is specifically BY-Mono.

In the above method, the encoding gene of BbTPS3 can be introduced into BY-Mono through a recombinant plasmid pESC-Leu::BbTPS3; and the recombinant plasmid pESC-Leu::BbTPS3 is obtained by constructing the Bbtps3 gene shown in SEQ ID NO: 1 at the BamHI site of a pESC-Leu vector, and the rest sequence of the pESC-Leu vector remains unchanged.

DETAILED DESCRIPTION OF THE INVENTION

Figure 1:
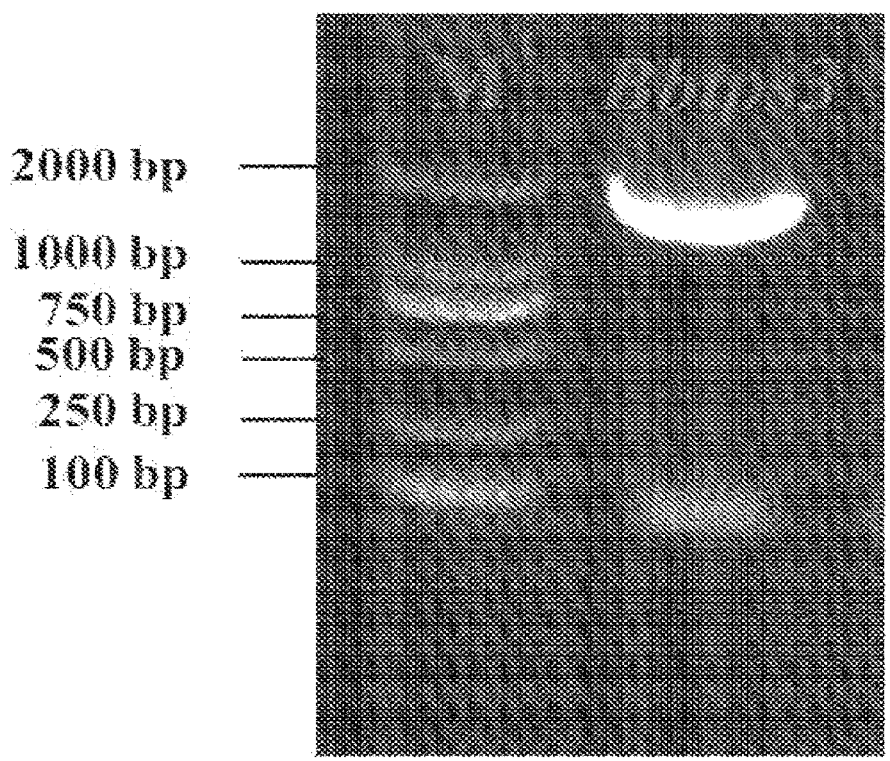
FIG. 1 is the agarose gel electrophoretogram of Bbtps3 gene of *Blumea balsamifera* (L.) DC., wherein M represents Trans2K DNA Marker (a nucleic acid molecular weight standard, with bands being 2000 bp, 1000 bp, 750 bp, 500 bp, 250 bp and 100 bp from top to bottom, respectively), and Bbtps3 represents Bbtps3 gene.

The present invention is further described in detail hereinafter with reference to specific embodiments, and the given examples are only used to illustrate the present invention, and are not intended to limit the scope of the present invention. The experimental methods in the following examples are all conventional methods unless otherwise specified. All the materials and reagents used in the following examples are commercially available unless otherwise specified.

The Phusion® High-Fidelity DNA Polymerase and the restriction endonuclease BamHI in the following examples are products of New England Biolabs Company.

Quick RNA isolation kit is a product of Huayueyang Biotechnology (Beijing) Co., Ltd.

TransScript One-Step gDNA Removal and cDNA Synthesis SuperMix, Trans2K DNA Marker, pEASY-Uni Seamless Cloning and Assembly Kit and *Escherichia coli* competent cell Transetta (DE3) are products of Beijing TransGen Biotech Co., Ltd.

Premixed Protein Marker (Low) is a product of Takara Company.

pET32a(+) vector is a product of Novagen Company.

pESC-Leu vector is a product of Agilent Company.

SD-Ura and SD-Ura-Leu are products of Beijing FunGenome Company.

ZYMO RESEARCH Frozen-EZ Yeast Transformation II kit is a product of Zymo Research Company.

BY4741 yeast strain (genotype: MATa his3Δ1 leu2Δ0 met15Δ0 ura3Δ0) is purchased from Huayueyang Biotechnology (Beijing) Co., Ltd.

Geranyl pyrophosphate (GPP) is a product of Sigma Company, with a product catalog number G6772 and a CAS number 763-10-0.

l-Borneol ((−)-borneol) is a product of Sigma Company, with a product catalog number CRM40456 and a CAS number 464-45-9.

Example 1 Full-Length cDNA Sequence Clone of Bbtps3 Gene of *Blumea balsamifera* (L.) DC 1. Extraction of Total RNA According to the instructions of the Quick RNA isolation kit of Huayueyang Biotechnology (Beijing) Co., Ltd., the total RNA of *Blumea balsamifera* leaves was extracted.

2. Synthesis of First-Strand cDNA

According to the instructions of the first-strand cDNA synthesis kit TransScript One-Step gDNA Removal and cDNA Synthesis SuperMix of Beijing TransGen Biotech Co., Ltd., the cDNA was obtained by reverse transcription.

| The reverse transcription reaction system was as follows: | |
|---|---|
| Total RNA | 5.0 μg |
| Anchored Oligo(dT)$_{18}$ Primer | 1.0 μL |
| 2 × TS Reaction Mix | 10.0 μL |
| TransScript ® RT/RI Enzyme Mix | 1.0 μL |
| gDNA Remover | 1.0 μL |
| RNase-free Water | added to a final volume of 20.0 μL |
| Total volume | 20.0 μL |

The steps of reverse transcription were as follows:

(1) in order to improve the synthesis efficiency, the total RNA, Anchored Oligo(dT)$_{18}$ Primer and RNase-free Water were evenly mixed in a PCR tube at 65° C. for 5 minutes;

(2) 10.0 μL of 2×TS Reaction Mix, 1.0 μL of TransScript RT/RI Enzyme Mix and 1.0 μL of gDNA Remover were added into the above PCR tube, and mixed evenly and gently;

(3) the reverse transcription reaction was performed at "42° C. for 30 minutes, 85° C. for 5 seconds" to obtain the first-strand cDNA;

(4) the first-strand cDNA was stored at −20° C.

3. Design of Primers

According to the transcriptome data of *Blumea balsamifera* leaves, the open reading frame (ORF) sequence was obtained. Based on this, cloning primers BbTPS3-F1 and BbTPS3-R1 were designed. The sequences of the primers were as follows:

BbTPS3-F1:
5'-ATGGTTGGATTTCAAAAACACTCATG-3';

BbTPS3-R1:
5'-CTAGGTTTTAGGCTTCAAAAGTAATGAGT-3'

4. PCR Amplification

The PCR amplification was performed with high-fidelity enzyme Phusion® High-Fidelity DNA Polymerase, with the first-strand cDNA obtained in step 2 as template, as well as BbTPS3-F1 and BbTPS3-R1 are primers. The results are shown in FIG. 1. The PCR amplification product was sequenced.

The PCR amplification procedure was as follows:

PCR reaction procedure: pre-denaturation at 98° C. for 3 minutes; 35 cycles of (98° C. for 20 seconds, 55° C. for 20 seconds, 72° C. for 1 minute); and extension at 72° C. for 5 minutes.

Sequencing results show that: the sequence of the PCR amplification product is consistent with SEQ ID NO: 1, the gene shown in SEQ ID NO: 1 is named Bbtps3, which encodes a protein consisting of 556 amino acid residues, wherein the protein is named as BbTPS3 and the amino acid sequence of the protein is shown in SEQ ID NO: 2.

Example 2 Acquisition and Functional Analysis of BbTPS3 of *Blumea balsamifera* (L.) DC I. Acquisition of BbTPS3 Protein of *Blumea balsamifera* (L.) DC.

1. Construction of Recombinant Vector

The Bbtps3 gene shown in SEQ ID NO: 1 was inserted at the BamHI restriction enzyme site of the pET32a(+) vector (Novagen Company) by using the pEASY-Uni Seamless Cloning and Assembly Kit of Beijing TransGen Biotech Co., Ltd., and the rest sequence of the pET32a(+) vector remains unchanged to obtain a recombinant plasmid pET32a::BbTPS3.

Specific steps were as follows:

1) the PCR amplification product obtained in Example 1 was used as template, PCR amplification was performed with primers BbTPS3-F2 and BbTPS3-R2, finally, the purified PCR product was obtained through recovering and purifying steps. The sequences of the primers were as follows (the underlined sequences were vector homologous regions):

BbTPS3-F2:
5'-CCATGGCTGATATCGGAATGGTTGGATTTCAAAAACACTCA-3';

BbTPS3-R2:
5'-ACGGAGCTCGAATTCGGCTAGGTTTTAGGCTTCAAAAGTA-3';

2) the pET32a(+) vector (Novagen Company) was digested with the restriction endonuclease BamHI, and then the linearized vector backbone was recovered;

3) according to the instructions of the pEASY-Uni Seamless Cloning and Assembly Kit of Beijing TransGen Biotech Co., Ltd., the purified PCR product obtained in step 1) was combined with the linearized vector backbone in step 2) to obtain a recombinant plasmid pET32a::BbTPS3.

2. Acquisition of Recombinant Bacteria

The recombinant plasmid pET32a::BbTPS3 was transformed into expression strain *Escherichia coli* Transetta (DE3) (purchased from Beijing TransGen Biotech Co., Ltd.) to obtain pET32a::BbTPS3 recombinant bacteria. Meanwhile, *E. coli* Transetta (DE3) was transformed with the pET32a(+) vector without the target gene (i.e., the Bbtps3 gene) and this recombinant strain was used as control bacteria.

3. Acquisition of Recombinant Protein BbTPS3

The pET32a::BbTPS3 recombinant bacteria and the control bacteria were respectively inoculated into 2 mL of LB liquid medium (containing 100 mg/L ampicillin), shaken and cultured overnight at 37° C. The next day, the cells were diluted in 200 mL LB liquid medium in the ratio of 1:100, shaken and cultured at 37° C. until the $OD_{600}$ reached 0.6~0.8, and then shaken at 18° C. for 1 hour. IPTG was added to a final concentration of 0.5 mM, and the mixture was continuously cultured in a shaking table at 18° C. for 24 hours to induce the expression of the target protein. The bacterial solution was centrifuged at 8000 g for 5 minutes, the supernatant was discarded, the cells of pET32a::BbTPS3 recombinant bacteria and the control bacteria were collected, and stored at −80° C. for later use.

4. Purification of Recombinant Protein BbTPS3

The proteins in the pET32a::BbTPS3 recombinant bacteria and the control bacteria were extracted. Specific steps were as follows:

the pET32a::BbTPS3 recombinant bacteria and the control bacteria were resuspended with 5 mL of pre-cooled HEPES buffer (25 mM HEPES, 5 M $MgCl_2$, 5 M DTT, pH 7.0), sonication (at 30% power for 5 seconds by an interval of 5 seconds, which lasted for 5 minutes and was repeated once) in ice bath, and centrifuged at 12,000 g and 4° C. for 30 minutes to obtain the supernatant protein solutions of the pET32a::BbTPS3 recombinant bacteria and the control bacteria respectively.

Figure 2:
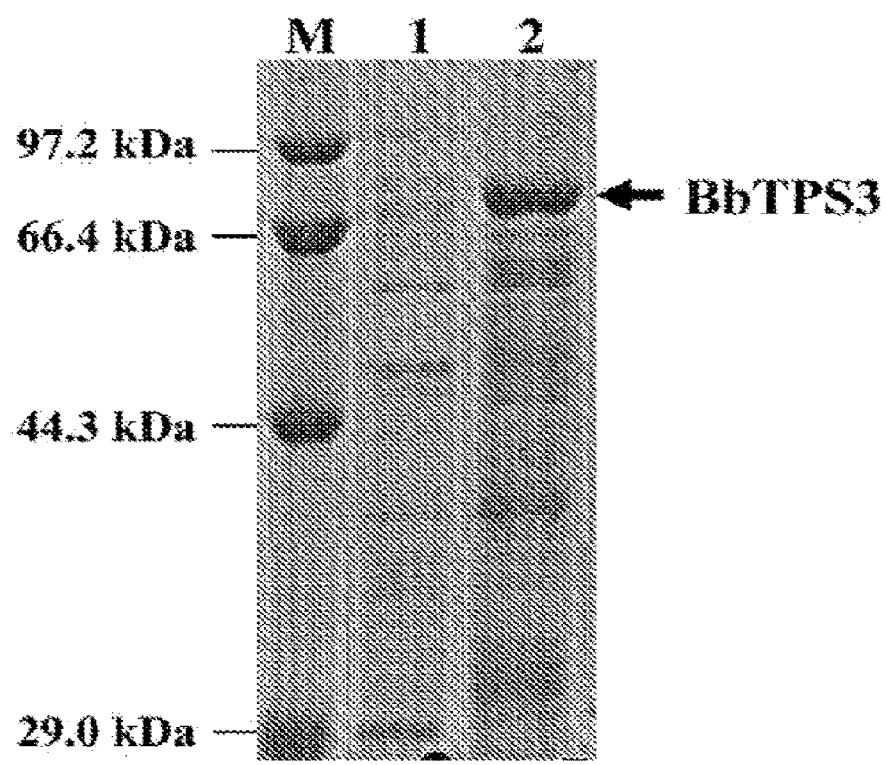
FIG. 2 shows the polyacrylamide gel electrophoresis (SDS-PAGE) analysis of BbTPS3 protein expressed in *Escherichia coli*, wherein M represents Premixed Protein Marker (Low) (a protein molecular weight standard, with bands being 97.2 KDa, 66.4 KDa, 44.3 KDa and 29.0 KDa from top to bottom, respectively), lane 1 represents the electrophoresis result of the supernatant of the control bacteria, lane 2 represents the electrophoresis result of the supernatant of the pET32a::BbTPS3 recombinant bacteria, and BbTPS3 represents the target protein expressed by the recombinant plasmid pET32a::BbTPS3 (i.e., the recombinant protein BbTPS3).

SDS-PAGE was performed on the supernatant of the pET32a::BbTPS3 recombinant bacteria and the supernatant of the control bacteria. The results are shown in FIG. 2. It can be seen from the figure that the recombinant plasmid pET32a::BbTPS3, which contains the protein BbTPS3 could be expressed in the supernatant of the pET32a::BbTPS3 recombinant bacteria, and the size of the recombinant protein BbTPS3 is about 82.5 kDa, which is consistent with the expected size. The supernatant of the control bacteria has no corresponding protein.

II. Enzymatic Activity Analysis of Recombinant Protein BbTPS3

1. Enzymatic Reaction

An enzymatic reaction was performed with the supernatant of the pET32a::BbTPS3 recombinant bacteria, and to obtain an enzymatic reaction product. The specific steps of the enzymatic reaction were as follows:

the total enzymatic reaction system was 0.2 mL; including 190 μL of the supernatant of the pET32a::BbTPS3 recombinant bacteria (the supernatant of the pET32a::BbTPS3 recombinant bacteria contained an enzymatic buffer, which was namely the HEPES buffer (25 mM HEPES, 5 M $MgCl_2$, 5 M DTT, pH 7.0)) and 10 μL of geranyl pyrophosphate (GPP) as a substrate. After evenly mixing, the overall enzymatic reaction system was sealed with 200 μL of n-hexane covering solution and placed at 30° C. for 2 hours; the n-hexane in the water phase was thoroughly removed under a stream of nitrogen (to avoid affecting the dephosphorylation reaction of the next step) to obtain an enzymatic reaction product of the supernatant of the pET32a::BbTPS3 recombinant bacteria.

2. Dephosphorylation Reaction

A dephosphorylation reaction system was prepared, fully mixed (blown with a pipette), and dephosphorylated at 37° C. for 4 hours to obtain a dephosphorylated product.

The dephosphorylation reaction system was as follows:

| | |
|---|---|
| Water phase (enzymatic reaction product of the supernatant of pET32a::BbTPS3 recombinant bacteria) | 200 μL |
| 10 × CutSmart Buffer | 22 μL |
| CIP | 2 μL |

The dephosphorylated product was extracted with n-hexane for three times, 0.2 mL each time, and the extracted organic phases were pooled together. The extracting solution was blow-dried with nitrogen, and added with 100 μL of n-hexane for dissolution to obtain the target compound (which was namely the target compound of the supernatant of the pET32a::BbTPS3 recombinant bacteria) for GC-MS analysis.

3. GC-MS Analysis

Gas chromatography-mass spectrometry GC-MS was used to detect the target compound of the supernatant of the pET32a::BbTPS3 recombinant bacteria: the GC-MS analysis system was Thermo TRACE 1310/TSQ 8000 gas chromatograph, with an injection volume of 1 μL, a mode of splitless, a gas chromatographic column of Agilent J&W Cyclodex-B chiral column (30 m×0.25 mm×0.25 μm) was used. And helium was used as carrier gas with flow rate of 1.0 mL/min. The injection port temperature was 220° C. and ion source temperature of 200° C., a heating program was following: hold at 50° C. for 2 minutes, increased from 50° C. to 150° C. by 3° C. min' and hold 150° C. for 5 minutes, then increased to 220° C. by 10° C. min'. Ionization energy was set at 70 eV, and the sample was scanned in a range of 50 m/z to 500 m/z.

190 μL of the supernatant of the pET32a::BbTPS3 recombinant bacteria in the above reaction was replaced by 190 μL of the supernatant of the control bacteria, and the above experiment was repeated to obtain the target compound of the supernatant of the control bacteria.

Figure 3:
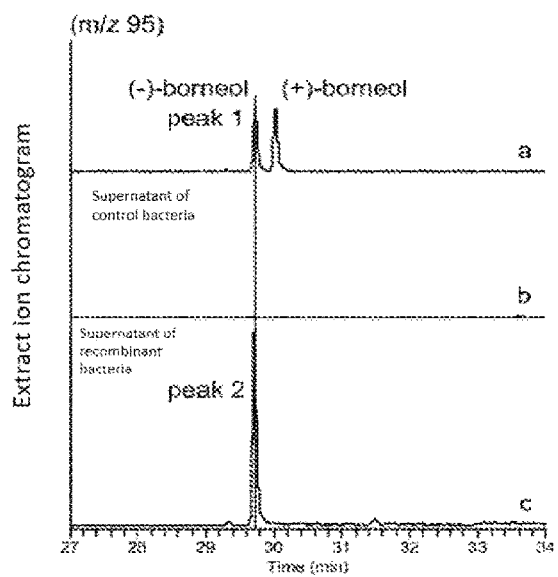
FIG. 3 shows the GC-MS analysis of the enzymatic reaction product of BbTPS3, wherein, in panel A, a represents the extract ion chromatogram of standard (−)-borneol and standard (+)-borneol, b represents the extract ion chromatogram of the target compound in the supernatant of the control bacteria, and c represents the extract ion chromatogram of the target compound in the supernatant of the pET32a::BbTPS3 recombinant bacteria; panel B represents the mass spectrum of standard (−)-borneol; and panel C represents the mass spectrum of the target compound in the supernatant of the pET32a::BbTPS3 recombinant bacteria.
Figure 3:
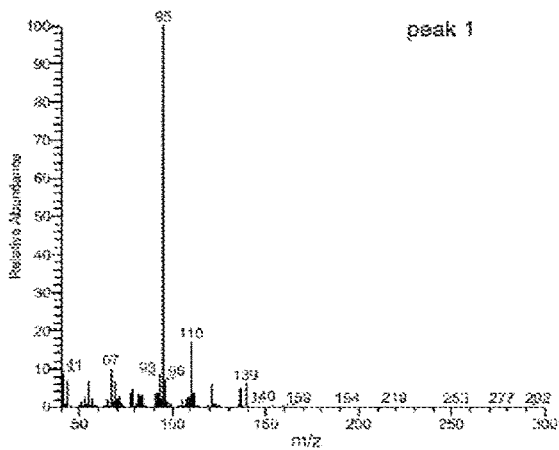
Figure 3:
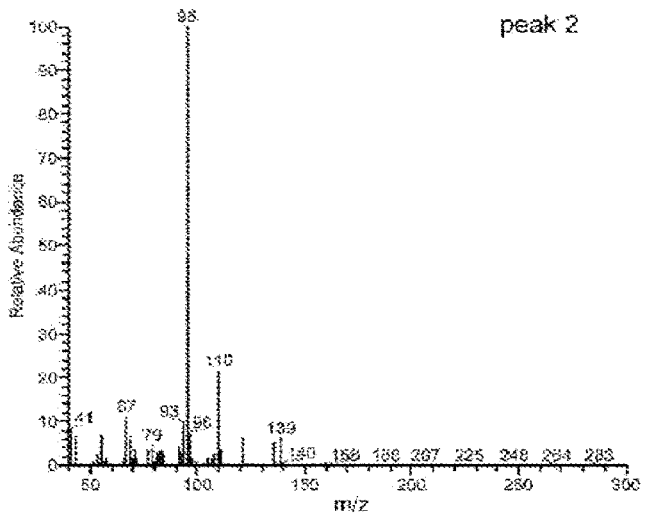

The results of the GC-MS analysis are shown in FIG. 3: (−)-borneol was not detected in the target compound of the supernatant of the control bacteria, but was detected in the target compound of the supernatant of the pET32a::BbTPS3 recombinant bacteria, indicating that the recombinant protein BbTPS3 can catalyze the formation of (−)-borneol from GPP, i.e. the recombinant protein BbTPS3 is a monoterpene synthase.

Example 3 Introduction of *Blumea balsamifera* BbTPS3 into Yeast Strain for Fermenting and Producing (−)-Borneol 1. Construction of Eukaryotic Expression Vector The Bbtps3 gene shown in SEQ ID NO: 1 was insert at the BamHI restriction enzyme site of the pESC-Leu vector (Agilent Company) by using the pEASY-Uni Seamless Cloning and Assembly Kit of Beijing TransGen Biotech Co., Ltd., and the rest sequence of the pESC-Leu vector remains unchanged to obtain a recombinant plasmid pESC-Leu::BbTPS3.

Specific steps were as follows:

1) the PCR amplification product obtained in Example 1 was used as a template, PCR amplification was performed with primers BbTPS3-F3 and BbTPS3-R3, and the purified PCR product was obtained through recovering and purifying steps; the sequences of the primers were as follows (the underlined sequences were vector homologous regions):

BbTPS3-F3:
5'-AAGGAGAAAAAACCCCGATGGTTGGATTTCAAAAACACTC-3';

BbTPS3-R3:
5'-AGTGAGTCGTATTACGGCTAGGTTTTAGGCTTCAAAAGTA-3';

2) the pESC-Leu vector was digested with the restriction endonuclease BamHI, and then the linearized vector backbone was recovered;

3) according to the instructions of the pEASY-Uni Seamless Cloning and Assembly Kit of Beijing TransGen Biotech Co., Ltd., the purified PCR product obtained in step 1) was combined with the linearized vector backbone in step 2) to obtain a recombinant plasmid pESC-Leu::BbTPS3.

2. Construction of BY-Mono Yeast Strain

YPD solid medium: 1% of yeast extract+2% of peptone+2% of glucose+1.5% of agar; the corresponding liquid medium (YPD liquid medium) was prepared without adding the agar.

YPL induction medium: 1% of yeast extract+2% of peptone+2% of galactose.

SD-Ura solid plate: SD-Ura+2% of glucose+2% of agar; the corresponding liquid medium (SD-Ura liquid medium) was prepared without adding the agar.

SD-Ura-Leu solid plate: SD-Ura-Leu+2% of glucose+2% of agar; the corresponding liquid medium (SD-Ura-Leu liquid medium) was prepared without adding the agar.

BY4741 yeast strain (genotype: MATa his3Δ1 leu2Δ0 met15Δ0 ura3Δ0) was coated on the YPD solid plate, and cultured upside down at 30° C. for 48 hours to 72 hours to obtain a newly activated BY4741 yeast colony. Ura3 marker, yeast-derived tHMGR1 (containing promoter sequence $P_{TDH3}$ and terminator sequence $T_{TPI1}$, which was namely $P_{TDH3}$-tHMGR1-$T_{TPI1}$), yeast-derived IDI1 (containing promoter sequence $P_{ADH1}$ and terminator sequence $T_{PGI}$, which was namely $P_{ADH1}$-IDI1-$T_{PGI}$), yeast-derived tHMGR1 (containing promoter sequence $P_{PGK1}$ and terminator sequence $T_{ADH1}$, which was namely $P_{PGK1}$-tHMGR1-$T_{ADH1}$), and yeast-derived ERG20$^{F96W-N127W}$ (containing promoter sequence $P_{TEF2}$ and terminator sequence $T_{CYC1}$, which was namely $P_{TEF2}$-ERG20$^{F96W-N127W}$-$T_{CYC1}$) were integrated at the YPRCΔ15 site (chromosome XVI long_terminal_repeat and Autonomously Replicating Sequence, YPRCΔ15) of the BY4741 yeast strain. Specific steps were as follows:

1) inoculated 5 ml of YPD with an aliquot of an overnight culture or a colony from a BY4741 fresh plate, grew at 30° C. and 200 rpm until $OD_{600}$ of 0.6 to 1.0;

2) taken a cuvette (0.2 cm) soaked in ethanol and then be cleaned with ultra-pure water and air-dried, put upside down on filter paper, and finally placed in an ultra-clean table for sterilization;

3) harvested 1 mL to 2 mL solution at 10,000 g for 1 minute at room temperature;

4) washed by resuspending the pellet in 1 ml of ice-cold sterile water, and centrifuged as above;

5) repeated step 4) and discarded the supernatant, resuspended in 1 ml of ice-cold buffer (10 mM LiAc, 10 mM DTT, 0.6 M sorbitol, and 10 mM Tris-HCl (pH 7.5)), and cultured at 25° C. for 20 minutes;

6) centrifuged as above and discarded the supernatant;

7) resuspended in 1 mL of ice-cold sorbitol (1 M), and centrifuged as above;

8) repeated step 7) and discarded the supernatant. Resuspended cells in 100 μL of ice-cold sorbitol (1 M) solution and then BY4741 yeast competent cells were prepared;

9) five DNA fragments of Ura3 marker, $P_{TDH3}$-tHMGR1-$T_{TPI1}$, $P_{ADH1}$-IDI1-$T_{PGI}$, $P_{PGK1}$-tHMGR1-$T_{ADH1}$ and $P_{TEF2}$-ERG20$^{F96W-N127W}$-$T_{CYC1}$ were mixed in equal molar ratio, with a total mass of 500 ng (the total volume was no more than 1/10 of the volume of the competent cells), added into the BY4741 yeast competent cells, mixed and transferred to an cuvette (0.2 cm), and incubated on ice for 2 minutes to 5 minutes; electrotransformation was performed under 2.7 kV, 25 µF and 200Ω (Bio-Rad, Hercules, Calif.), and after electric shock, added 1 mL of sorbitol (1 M) solution in an ultra-clean working table, then transferred into a sterile 1.5 mL EP tube, cultured at 30° C. for 1 to 2 hours, and mixed up and down for 2 to 3 times;

10) the mixture was centrifuged at 10,000 g for 1 minute at room temperature, discard the supernatant, and the cells were resuspended with the remaining 100 µL of solution; the solution was dropwise added in the center of the synthetic dropout medium SD-Ura solid plate, evenly coated by using a coater until all the coated solution was completely absorbed, and placed in an incubator at 30° C. for inverted culture for 2 to 3 days; the obtained strain was named as BY-Mono yeast strain, and the genotype of BY-Mono yeast was MATa his3Δ1 leu2Δ0 met15Δ0 ura3Δ0, YPRCΔ15 Ura3-$P_{TDH3}$-tHMGR1-$T_{TPI1}$-$P_{ADH1}$-IDI1-$T_{PGI}$-$P_{PGK1}$-tHMGR1-$T_{ADH1}$-$P_{TEF2}$-ERG20$^{F96W-N127W}$-$T_{CYC1}$.

3. Preparation of BY-Mono Yeast Competent Cells

Yeast competent cells were prepared by using the ZYMO RESEARCH Frozen-EZ Yeast Transformation II kit:

(1) picked the refresh BY-Mono single colony from the SD-Ura plate, inoculated into 10 mL of SD-Ura liquid medium, and shaken and cultured at 30° C. until OD$_{600}$ of 0.8 to 1.0;

(2) pelleted the cells at 500 g for 4 minutes and discarded the supernatant.

(3) added 10 mL of Frozen-EZ Solution 1 to wash pellet, and centrifuged as above, and discarded the supernatant;

(4) added 1 mL of Frozen-EZ Solution 2 to resuspend the pellet to obtain the BY-Mono yeast competent cells, and the BY-Mono yeast competent cells were sub-packaged into sterile 1.5 mL EP tubes, with 50 µL in each tube;

(5) BY-Mono competent cells were slowly cooled to −70° C. (4° C. for 1 hour; −20° C. for 1 hour; −40° C. for 1 hour; stored at −70° C.), and it was forbidden to quick freeze the competent cells with liquid nitrogen.

4. Transformation of Plasmid pESC-Leu::BbTPS3 into BY-Mono Competent Cells (1) Mixed 50 µL of BY-Mono yeast competent cells with 0.2-1 µg plasmid pESC-Leu::BbTPS3 (in less than 5 µL).

(2) Added 500 µL of Frozen-EZ Solution 3, and mixed thoroughly.

(3) Incubated at 30° C. for 1 to 2 hours, and mix for 2 to 3 times.

(4) Spreaded 50-150 µL of the above transformation mixture on the SD-Ura-Leu solid plate, air-dried, and then invertedly incubated at 30° C. for 48 to 96 hours to obtain a recombinant yeast transformed with the recombinant plasmid pESC-Leu::BbTPS3, which was named as BY-Mono/pESC-Leu::BbTPS3.

Meanwhile, the pESC-Leu vector without the target gene (which was namely the Bbtps3 gene) was transformed into the BY-Mono yeast competent cells by the same method as above and used as a control, to obtain a recombinant yeast transformed with the pESC-Leu vector, which was named as BY-Mono/pESC-Leu.

5. Fermentation (1) The BY-Mono/pESC-Leu::BbTPS3 single colony grown on the SD-Ura-Leu solid plate in step 4 was picked, and inoculated in 10 mL of SD-Ura-Leu liquid medium at 200 rpm and 30° C. for 48 hours.

(2) Harvested the cells at 5,000×g and room temperature for 5 minutes, and resuspended the cells by 20 mL of YPL liquid medium, and cultured at 200 rpm and 30° C. for 72 hours to obtain a fermentation product.

6. Extraction of Fermentation Product

The target compound was terpenoid, which was fat-soluble and easily soluble in ethyl acetate. Therefore, ethyl acetate was selected as a solvent to extract the fermentation product, to obtain the target compound. The steps of the extraction were as follows:

(1) collected the fermented solution, which was the fermentation product, and added with an equal volume of ethyl acetate;

(2) sonicated the above mixture for 1 hour, and shaken and mixed for many times during this period;

(3) the upper organic phase was taken at 5,000×g at room temperature for 5 minutes, added in an appropriate amount of anhydrous sodium sulfate (dried at 120° C. for 30 minute), and shaken during addition to remove the water in the extract;

(4) the solution was concentrated on rotary evaporator to be nearly dry;

(5) the concentrated solution was pipetted, and filtered through a 0.22 µm PTFE needle filter, and the filtrate was stored in vial, sealed with a sealing film, and stored in a refrigerator at 4° C.

7. GC-MS Detection of Fermentation Product

Gas chromatography-mass spectrometry GC-MS was used to detect the target compound: the GC-MS analysis system was Thermo TRACE 1310/TSQ 8000 gas chromatograph, with an injection volume of 1 µL, a mode of splitless. A gas chromatographic column of Thermo Scientific TG-5MS (30 m×0.25 mm×0.25 µm) was used. And helium was used as carrier gas with flow rate of 1.0 mL/min. The injection port temperature was 220° C. and ion source temperature of 200° C., a heating program was following: hold at 50° C. for 2 minutes, increased from 50° C. to 150° C. by 5° C.·min$^{-1}$ and hold 150° C. for 2 minutes, then increased to 300° C. by 30° C.·min$^{-1}$. Ionization energy was set at 70 eV, and the sample was scanned in a range of 50 m/z to 500 m/z.

In the fermentation of the above step 5, "the BY-Mono/pESC-Leu::BbTPS3 single colony grown on the SD-Ura-Leu solid plate in step 4 was picked" was replaced by "the BY-Mono/pESC-Leu single colony grown on the SD-Ura-Leu solid plate in step 4 was picked", and the above experiment steps 5, 6 and 7 were repeated.

Figure 4:
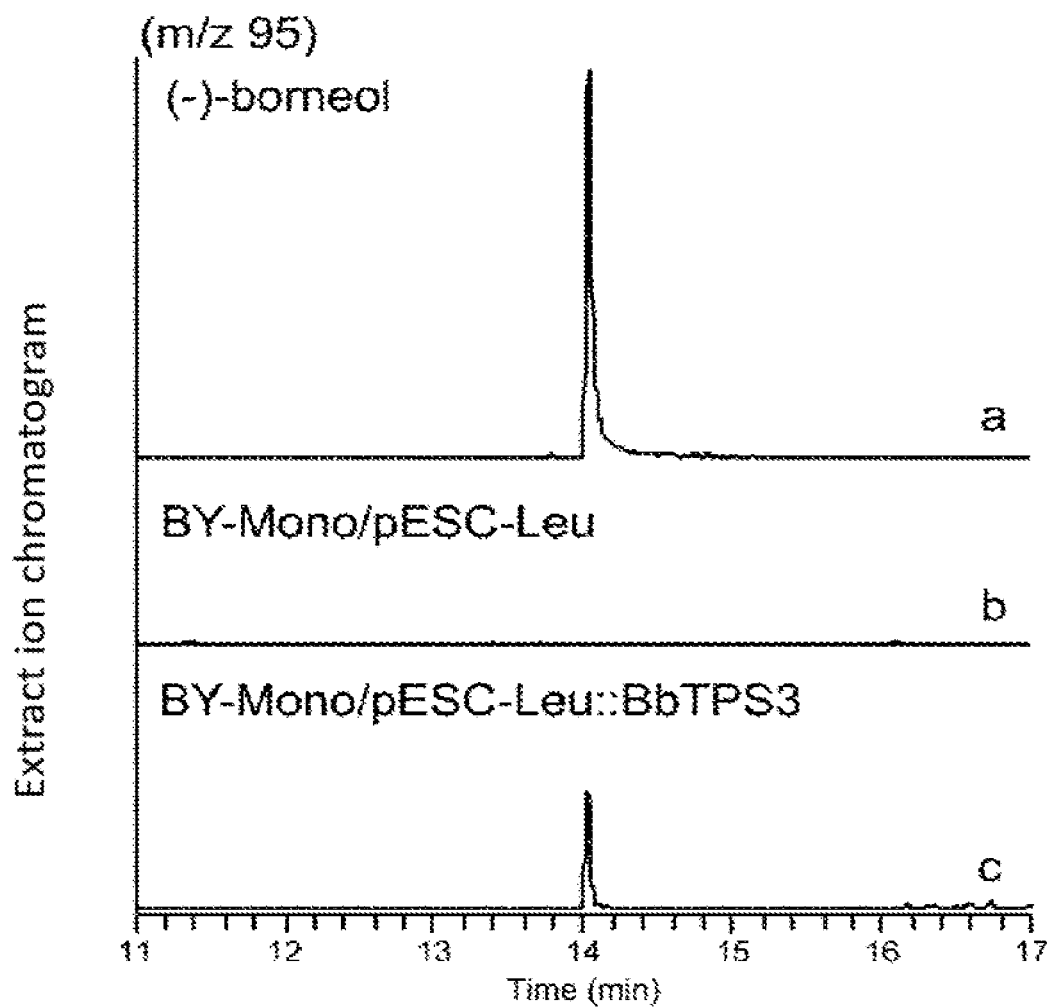
FIG. 4 shows the GC-MS analysis of (−)-borneol fermented and produced by introducing BbTPS3 into yeast strain (BY-Mono), wherein a represents the extract ion chromatogram of standard (−)-borneol, b represents the extract ion chromatogram of the target compound obtained by extracting the fermentation product of the recombinant yeast BY-Mono/pESC-Leu, and c represents the extract ion chromatogram of the target compound obtained by extracting the fermentation product of the recombinant yeast BY-Mono/pESC-Leu::BbTPS3.

The results of GC-MS analysis are shown in FIG. 4: the target compound obtained by extracting the fermentation product of the recombinant strain BY-Mono/pESC-Leu::BbTPS3 containing the plasmid pESC-Leu::BbTPS3 is (−)-borneol, which means that (−)-borneol can be synthesized by the recombinant BY-Mono/pESC-Leu::BbTPS3, and about 2.0 mg of (−)-borneol can be obtained from per liter of fermentation broth through statistics. (−)-Borneol is not detected in the target compound obtained by extracting the fermentation product of the recombinant strain BY-Mono/pESC-Leu containing the pESC-Leu vector.

The present invention is described in detail above. For those technicians in the field, the present invention can be implemented in a wide range under equivalent parameters, concentrations and conditions without departing from the purpose and scope of the present invention and unnecessary experiments. Although the present invention gives specific examples, it should be understood that the present invention can be further improved. In a word, according to the principle of the present invention, the present application is intended to comprise any changes, uses or improvements of the present invention, comprising changes that deviate from the scope disclosed in the present application but are made by conventional techniques known in the art. According to the scope of the following appended claims, some basic features can be applied.

INDUSTRIAL APPLICATION

The Bbtps3 gene is cloned from the cDNA of *Blumea balsamifera* (L.) DC. in the present invention, and the gene is a key enzyme gene for the synthesis of a monoterpene ingredient obtained from *Blumea balsamifera* (L.) DC. for the first time. It has been proved by experiments that: the BbTPS3 protein mentioned in the present invention can catalyze the formation of (−)-borneol (l-borneol) from GPP, and has an important role in the biosynthesis of (−)-borneol and other monoterpene compounds in *Blumea balsamifera* (L.) DC., and provides an important basis for increasing the content of the active ingredient (−)-borneol in *Blumea balsamifera* (L.) DC. by using a genetic engineering technology or directly producing (−)-borneol, thus further having important theoretical and practical significances for regulating and producing plant monoterpene compounds and culturing high-quality *Blumea balsamifera* (L.) DC.

The invention claimed is:

1. An isolated monoterpene synthase, wherein the protein is:
   A1) a protein having the amino acid sequence shown in SEQ ID NO: 2; or
   A2) a fusion protein obtained by linking protein-tags at the N-terminus or/and the C-terminus of the protein shown in SEQ ID NO: 2; or
   A3) a protein having at least 98% or 99% identity and the same function as the protein shown in A1), which is obtained by performing substitution and/or deletion and/or addition of one or more amino acid residues on the amino acid sequence shown in SEQ ID NO: 2.

2. An isolated nucleic acid molecule encoding the protein according to claim 1.

3. The nucleic acid molecule according to claim 2, wherein the nucleic acid molecule is a DNA molecule shown in SEQ ID NO: 1.

4. A method for preparing the protein according to claim 1, wherein the method comprises the steps of: introducing the encoding gene of the protein according to claim 1 into a recipient microorganism to obtain a recombinant microorganism expressing the protein according to claim 1, and culturing the recombinant microorganism to express the protein according to claim 1.

5. A method for biosynthesizing (−)-borneol, wherein the method comprises the steps of: introducing the encoding gene of the protein according to claim 1 into *Saccharomyces cerevisiae* with elevated geranyl pyrophosphate synthesis to obtain recombinant *Saccharomyces cerevisiae*, and fermenting the recombinant *Saccharomyces cerevisiae* to obtain (−)-borneol.

6. A recombinant vector containing the nucleic acid molecule according to claim 2.

7. A recombinant microorganism containing the nucleic acid molecule according to claim 2.

8. A transgenic plant cell line containing the nucleic acid molecule according to claim 2.

* * * * *